United States Patent
Tokita et al.

(10) Patent No.: US 9,271,695 B2
(45) Date of Patent: Mar. 1, 2016

(54) APPARATUS FOR MAMMOGRAPHY WITH ACOUSTIC MATCHING

(75) Inventors: Toshinobu Tokita, Kyoto (JP); Yasuhiro Someda, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 13/512,662

(22) PCT Filed: Jan. 26, 2011

(86) PCT No.: PCT/JP2011/000414
§ 371 (c)(1),
(2), (4) Date: May 30, 2012

(87) PCT Pub. No.: WO2011/096174
PCT Pub. Date: Aug. 11, 2011

(65) Prior Publication Data
US 2012/0238859 A1    Sep. 20, 2012

(30) Foreign Application Priority Data
Feb. 2, 2010   (JP) .................................. 2010-021169

(51) Int. Cl.
*A61B 8/00*   (2006.01)
*A61B 8/08*   (2006.01)
*A61B 5/00*   (2006.01)

(52) U.S. Cl.
CPC ............. *A61B 8/0825* (2013.01); *A61B 5/0095* (2013.01); *A61B 8/4281* (2013.01)

(58) Field of Classification Search
CPC ... A61B 5/0095; A61B 8/4281; A61B 8/0825

USPC .................................................. 600/437, 476
See application file for complete search history.

(56) References Cited

U.S. PATENT DOCUMENTS

| 5,409,446 | A | 4/1995 | Rattner ............................. 601/4 |
| 5,474,072 | A | 12/1995 | Shmulewitz .................. 600/446 |
| 5,479,927 | A | 1/1996 | Shmulewitz .................. 600/445 |

(Continued)

FOREIGN PATENT DOCUMENTS

| CN | 1897879 | 1/2007 |
| EP | 0882426 | 12/1998 |

(Continued)

OTHER PUBLICATIONS

S. Manohar et al., "The Twente Photoacoustic Mammoscope: System Overview and Performance", *Physics in Medicine and Biology*, vol. 50, No. 11, pp. 2543-2557 (2005).

(Continued)

*Primary Examiner* — Long V Le
*Assistant Examiner* — Angela M Hoffa
(74) *Attorney, Agent, or Firm* — Fitzpatrick, Cella, Harper & Scinto (57) ABSTRACT

The present invention employs a measuring apparatus having: a holding plate for holding a subject; an acoustic matching member provided between the subject and the holding plate; and a probe for receiving an acoustic wave propagating through the subject via the acoustic matching member and the holding plate, wherein the acoustic matching member includes a first portion that contacts the subject and a second portion that contacts the holding plate, and the second portion has greater rigidity than the first portion.

13 Claims, 6 Drawing Sheets

(56) References Cited

U.S. PATENT DOCUMENTS

| | | | |
|---|---|---|---|
| 5,603,326 A | 2/1997 | Richter | 600/443 |
| 5,640,956 A * | 6/1997 | Getzinger et al. | 600/427 |
| 5,664,573 A | 9/1997 | Shmulewitz | 128/660.09 |
| 5,833,627 A * | 11/1998 | Shmulewitz et al. | 600/562 |
| 5,851,180 A * | 12/1998 | Crosby et al. | 600/407 |
| 5,938,613 A * | 8/1999 | Shmulewitz | 600/461 |
| 6,117,080 A | 9/2000 | Schwartz | 600/443 |
| 6,607,489 B2 * | 8/2003 | Hoctor et al. | 600/443 |
| 7,505,555 B2 * | 3/2009 | Hermann et al. | 378/37 |
| 7,756,246 B2 * | 7/2010 | Mikami et al. | 378/37 |
| 7,885,378 B2 * | 2/2011 | Kopans et al. | 378/21 |
| 8,317,702 B2 * | 11/2012 | Yu et al. | 600/437 |
| 8,480,584 B2 * | 7/2013 | Kanayama et al. | 600/437 |
| 8,540,637 B2 * | 9/2013 | Tokita et al. | 600/443 |
| 2005/0154308 A1 | 7/2005 | Quistgaard et al. | 600/459 |
| 2005/0154313 A1 * | 7/2005 | Desilets et al. | 600/459 |
| 2006/0074287 A1 * | 4/2006 | Neumann et al. | 600/407 |
| 2006/0241423 A1 | 10/2006 | Anderson et al. | 600/437 |
| 2008/0194959 A1 * | 8/2008 | Wang et al. | 600/445 |
| 2008/0255452 A1 * | 10/2008 | Entrekin | 600/444 |
| 2008/0269613 A1 * | 10/2008 | Summers et al. | 600/459 |
| 2008/0306371 A1 | 12/2008 | Fukutani et al. | 600/407 |
| 2009/0275837 A1 | 11/2009 | Shiina et al. | 600/459 |
| 2009/0299185 A1 | 12/2009 | Oikawa et al. | 600/447 |
| 2011/0230762 A1 | 9/2011 | Tokita et al. | 600/437 |
| 2011/0245666 A1 * | 10/2011 | Den Heeten et al. | 600/437 |
| 2011/0245667 A1 | 10/2011 | Tokita | 600/437 |
| 2011/0257530 A1 * | 10/2011 | Tokita et al. | 600/443 |
| 2012/0150012 A1 | 6/2012 | Fujimoto et al. | 600/407 |

FOREIGN PATENT DOCUMENTS

| | | |
|---|---|---|
| JP | 60-190853 | 9/1985 |
| JP | 2003-325523 | 11/2003 |
| JP | 1897879 | 1/2007 |
| JP | 2010-017427 | 1/2010 |
| WO | WO 99/56623 | 11/1999 |
| WO | WO 2004/030523 | 4/2004 |
| WO | WO 2009/009064 | 1/2009 |
| WO | WO 2009/022300 | 2/2009 |

OTHER PUBLICATIONS

Office Action issued on Dec. 27, 2013 in Chinese (PRC) counterpart application 01180007630.8, with translation.

JPO Office Action issued on Feb. 18, 2014 in Japanese counterpart application 2010-021169, with translation.

* cited by examiner

APPARATUS FOR MAMMOGRAPHY WITH ACOUSTIC MATCHING

TECHNICAL FIELD

The present invention relates to a measuring apparatus that receives an acoustic wave emitted from a subject.

BACKGROUND ART

A subject information acquisition apparatus (photoacoustic apparatus) developed to detect breast cancer is described in Non-Patent Literature 1 (NPL 1). In the apparatus described in NPL 1, a subject (a breast) is compressed between a glass plate and an acoustic wave probe, whereupon the breast is irradiated with illumination light (near-infrared light) using an Nd:YAG laser as a light source through the glass plate. An acoustic wave generated in the interior of the subject (the breast) is received by the acoustic wave probe, whereupon internal tissue of the subject (the breast), and in particular breast cancer angiogenesis, is reconstructed as an image and displayed.

With the apparatus of NPL 1, however, a gap may form between a part of the subject (the breast) and the acoustic wave probe, leading to lifting. The lifted part contains air, causing dramatic differences in acoustic impedance, and since the acoustic wave cannot pass through the lifted part, there results a region that cannot be subjected to image reconstruction.

Patent Literature (PTL) 1, 2 and 3 disclose methods for dealing with this type of lifting.

Figure 5A:
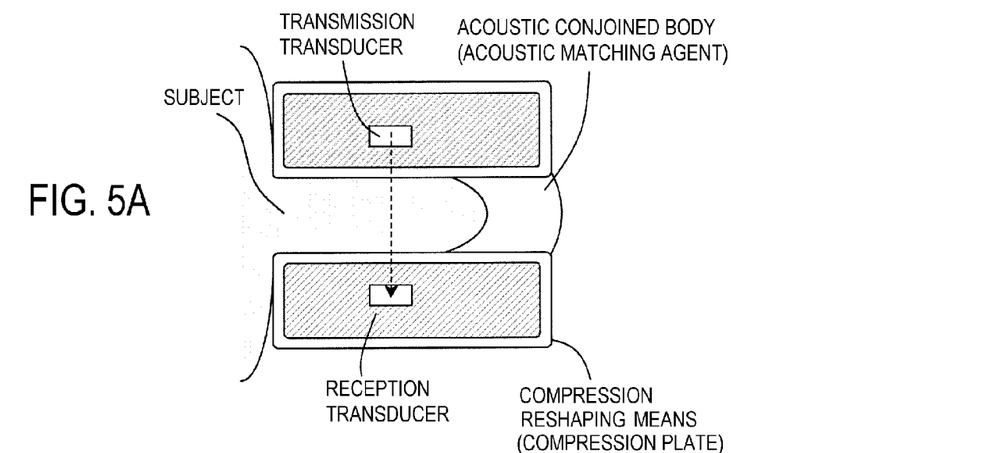
FIGS. 5A to 5C are views illustrating background art.
Figure 5B:
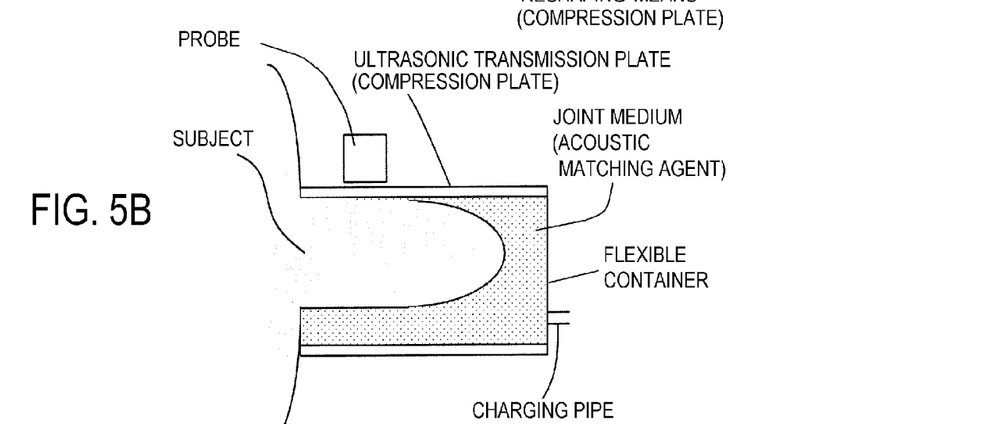
Figure 5C:
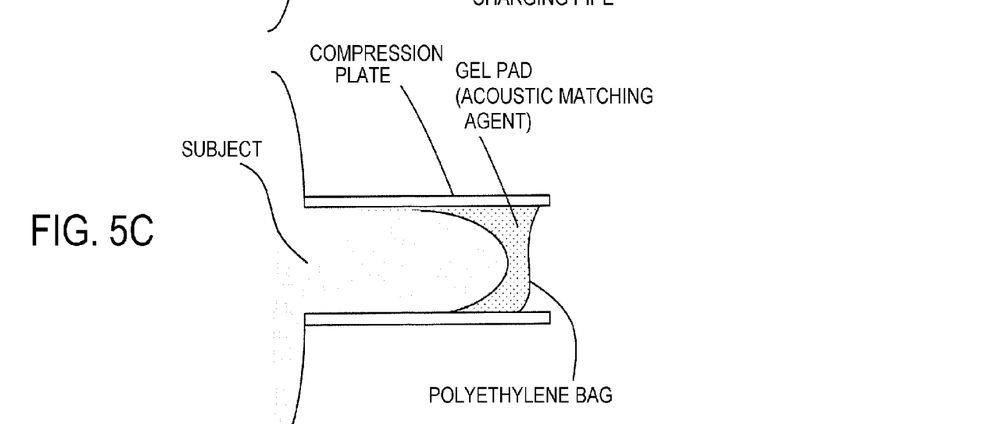

FIG. 5A shows an outline of PTL 1, in which an acoustic matching agent is filled between two compression plates for compressing a subject. FIG. 5B shows an outline of PTL 2. PTL 2 discloses a compression plate constituted by two plates for compressing a subject, an acoustic wave probe, and a flexible container for realizing acoustic matching. FIG. 5C shows an outline of PTL 3. PTL 3 similarly discloses a compression plate constituted by two plates and a gel pad provided between the two plates.

CITATION LIST

Patent Literature

[PTL 1]
Japanese Patent Application Laid-Open No. S60(1985)-190853
[PTL 2]
Japanese Translation of PCT Application No. H8(1996)-503156
[PTL 3]
Japanese Patent Application Laid-Open No. 2003-325523

Non-Patent Literature

[NPL 1]
Srirang Manohar et al., "The Twente photoacoustic mammoscope: system overview and performance", Physics in Medicine and Biology 50 (2005) 2543-2557

SUMMARY OF INVENTION

Technical Problem

However, the related art contains the following problems.

According to the technique of PTL 1, the problem of acoustic impedance matching can be alleviated, but when the same acoustic matching agent is used on a large number of subjects, a risk of infection or the like increases, and therefore strict hygienic management is required. Accordingly, the acoustic matching agent must be replaced for each subject, but the replacement operation takes time, leading to an increase in an operation time required to obtain an image.

With PTL 2, on the other hand, the labor required to replace an acoustic matching member can be omitted as long as the flexible container is kept clean. With PTL 3, the gel pad can be replaced comparatively easily.

However, with PTL 2, a gap forms between the subject and a probe side plate. To realize acoustic matching between the apparatus and the subject, it is necessary to envelop the subject, but in the state shown in FIG. 5B, lifting occurs at least between the subject and the probe side plate. Hence, the acoustic matching member is preferably provided between the subject and the probe side plate. However, the surface of the flexible container is highly flexible, and therefore, when the acoustic matching member is provided between the subject and the probe side plate, a folded back crease is likely to occur on a surface that contacts an acoustic wave transmission plate. Even when an acoustic matching agent such as sonar gel or water is used, it is not easy to plump out a crease sufficiently for air to be removed from the crease, and as a result, acoustic matching cannot be realized sufficiently.

When the gel pad of PTL 3 is constituted by sonar gel, air bubbles are likely to become intermixed into the gel pad, and since the air bubbles are difficult to remove, acoustic matching cannot be realized sufficiently. Further, when the gel pad is formed from an elastomer such as that of a stand-off typically used in acoustic wave diagnosis, a surface of the elastomer possesses flexibility, and therefore irregularities are likely to form on the surface. Air bubbles may enter the irregularities on the surface that contacts the compression plate, and since the air bubbles are difficult to remove, it may be impossible to realize acoustic matching sufficiently. Hence, although the problems of NPL 1 are alleviated, they cannot always be solved.

The present invention has been designed in consideration of the problems in the related art, and an object thereof is to provide an acoustic matching member for a measuring apparatus (a subject information acquisition apparatus) that can be replaced easily and is unlikely to entrap air.

Solution to Problem

This invention provides a measuring apparatus comprising:
a holding plate for holding a subject;
an acoustic matching member provided between the subject and the holding plate; and
a probe for receiving an acoustic wave propagating through the subject via the acoustic matching member and the holding plate,
wherein the acoustic matching member includes a first portion that contacts the subject and a second portion that contacts the holding plate, and the second portion has greater rigidity than the first portion.

Advantageous Effects of Invention

According to the present invention, an acoustic matching member for a measuring apparatus that can be replaced easily and is unlikely to entrap air can be provided.

Further features of the present invention will become apparent from the following description of exemplary embodiments with reference to the attached drawings.

DESCRIPTION OF EMBODIMENTS

In a measuring apparatus (a subject information acquisition apparatus), an acoustic wave (typically an ultrasonic wave) that propagates through and is emitted from a subject such as a living organism is received by a probe via a plate placed on the subject and then subjected to information processing in order to reconstruct an image (generate image data) of a subject interior. An acoustic matching member is provided between the subject and a probe-side plate. The acoustic matching member includes a part (a first portion) constituted by an elastomer or an elastomer enveloping a liquid, a sol, or a gel, and a layer (a second portion) having greater rigidity than the elastomer. The highly rigid layer forms a surface that contacts a plate of the apparatus.

Note that in the present disclosure, the term "acoustic wave" may include waves referred to as sound waves, ultrasonic waves, and photoacoustic waves, for example photoacoustic waves generated in the subject interior when the subject interior is irradiated with light such as near-infrared rays and ultrasonic waves transmitted to and received from the subject interior by an acoustic wave probe. In other words, the measuring apparatus (subject information acquisition apparatus) according to the present invention includes a photoacoustic apparatus that irradiates the subject interior with light, receives a photoacoustic wave generated by the subject interior in a probe, and generates image data, an ultrasonic wave apparatus that generates image data by transmitting and receiving ultrasonic waves, and so on.

Figure 4:
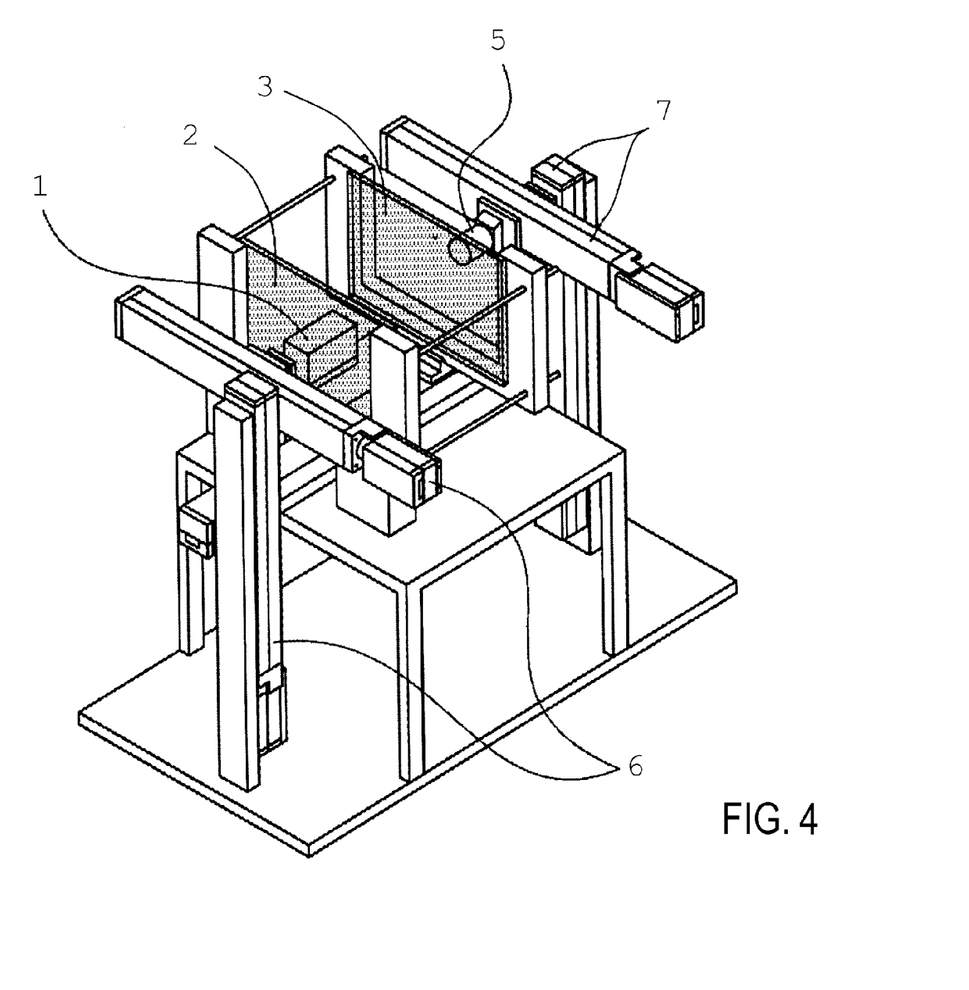
FIG. 4 is a view illustrating a subject information acquisition apparatus according to the present invention.

Photoacoustic mammography (to be abbreviated to "PAM" hereafter), in which measurement is performed in accordance with the principles of photoacoustic tomography (to be abbreviated to "PAT" hereafter), will now be described as an example of a subject information acquisition apparatus using FIG. 4. With PAT, images of blood and blood vessels can be captured specifically, and therefore cancer angiogenesis can be photographed. FIG. 4 shows a constitution of a PAM apparatus in which the principles of PAT are applied to a breast cancer examination.

In FIG. 4, a probe 1 receives an acoustic wave emitted from a subject (not shown) such as a breast. A holding plate 2 supports the subject in a constant shape, and in FIG. 4, the probe 1 receives the acoustic wave emitted by the subject via the holding plate 2. Polymethyl pentene ("PMP") is preferably used as the material of the holding plate 2, but another type of resin may be substituted. A compression plate 3 is formed to be movable so that a distance from the holding plate 2 can be adjusted, and the compression plate likewise keeps the shape (a surface on an opposite side to the holding plate) of the subject constant. By adjusting the distance between the two plates, the subject is supported while being compressed. A resin such as acryl or polycarbonate or a glass such as silica is preferably used as the material of the compression plate 3. An illumination optical system 5 irradiates the subject with pulsed light emitted from a light source (not shown) at a wavelength of approximately 650 nm to 1100 nm to cause the subject to generate acoustic waves. A probe scanning unit 6 causes the probe 1 to scan the subject in an in-plane direction of the holding plate. An illumination light scanning unit 7 causes the illumination optical system 5 to scan the subject in an in-plane direction of the compression plate.

Note, however, that in these embodiments, the probe 1 and the illumination optical system 5 may be provided in different positions to those of the above constitution. For example, the probe 1 may be provided on the compression plate side so as to scan the subject in the in-plane direction of the compression plate, and the illumination optical system 5 may be provided on the holding plate 2 side so as to scan the subject in the in-plane direction of the holding plate. Alternatively, the illumination optical system 5 may be provided on both the holding plate side and the compression plate side such that light is emitted from both surfaces.

Note that in the following examples, a photoacoustic apparatus will be described as an example of the subject information acquisition apparatus, but the present invention is not limited to this type of apparatus and may be applied to any apparatus in which an acoustic wave propagating through a subject is received by the probe 1 through a plate. For example, the present invention may be applied to an ultrasonic wave echo apparatus or a transmission type ultrasonic apparatus. In an ultrasonic wave echo apparatus, the probe 1 preferably transmits and receives beam-focused ultrasonic waves, and in a transmission type ultrasonic apparatus, a transmission probe is preferably provided in place of the illumination optical system 5. Note, however, that in this case, the acoustic matching member 4 must be provided between the compression plate 3 and the subject as well as between the holding plate 2 and the subject, and the compression plate must also be acoustically matched to the transmission probe. Further, PMP is preferably used as the material of the compression plate 3, similarly to the holding plate 2.

Further, the subject support method is not limited to compression support, and the present invention may be applied to any apparatus in which the probe 1 receives an acoustic wave via a plate. Furthermore, in each of the following examples, the acoustic matching member is provided on the holding plate side, but the present invention may be applied to any apparatus in which the acoustic matching member is provided between the plate on the side where the probe is provided and the subject.

Example 1

Outline of Apparatus

Figure 1A:
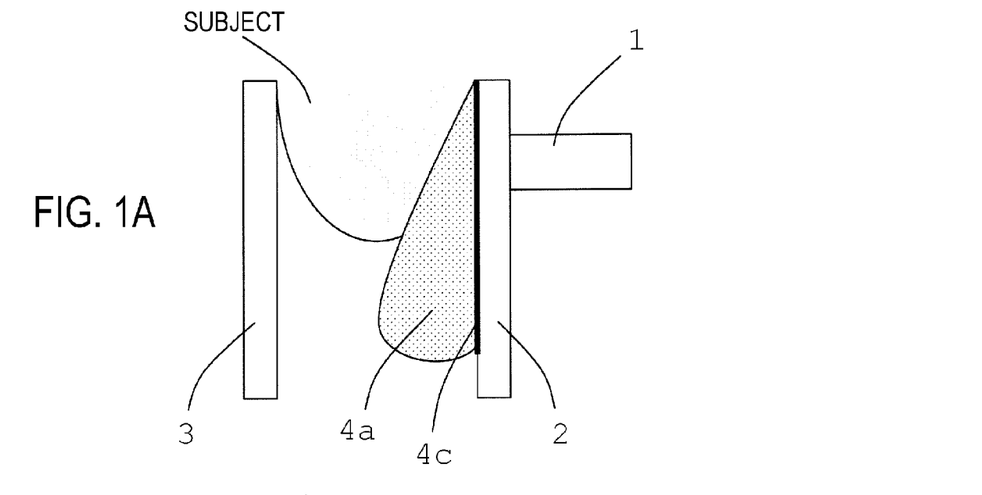
FIGS. 1A to 1D are views illustrating a constitution of an acoustic matching member according to a first example.

First, a first example will be described. FIG. 1A is a pattern diagram of a subject information acquisition apparatus according to this example. When measurement is performed using this apparatus, a patient lies face down so that the subject (a breast) is sandwiched between the compression plate and the holding plate. The probe 1 is capable of receiving acoustic waves generated by and propagating through the subject. When PAM is used, an acoustic wave (a photoacoustic wave) generated by the subject after being irradiated with light is received. The holding plate 2 supports the subject. The probe 1 receives an acoustic wave emitted by the subject through the holding plate 2. The probe 1 is capable of scanning the subject in the in-plane direction of the holding plate 2. An acoustic matching agent such as water or oil is provided between the probe 1 and the holding plate 2. The compression plate 3 can be moved to adjust the distance to the holding plate 2. By adjusting the distance in this manner, the subject is supported while being compressed.

In FIG. 1A, an acoustic matching member 4 is constituted by a water bag 4a and a sheet 4c. The water bag 4a contacts the subject, and the sheet 4c is positioned between the water bag 4a and the holding plate.

The water bag 4a is formed by forming a sheet-form elastomer such as urethane rubber having a thickness of approximately 30 μm (micrometer) into a bag shape to obtain a hollow portion and filling the hollow portion with a material capable of realizing acoustic matching. A liquid such as water, a sol, a gel, and so on, for example, may be used as the material filled into the hollow portion. Note, however, that the material and thickness of the water bag and the substance enclosed therein are not limited to these examples. The elastomer cited here is preferably a material that is capable of a large amount of restoration following deformation, exhibits behavior close to that of an incompressible material, and typically has a Poisson's ratio close to 0.5.

The film-form sheet 4c is an elastic body having greater rigidity, or in other words a higher Young's modulus, and a smaller Poisson's ratio than the water bag 4a (urethane rubber, for example). Polymethyl pentene ("PMP" hereafter) film having a thickness of several tens of micrometers is preferably used as the sheet 4c. Note, however, that a resin other than PMP may be used as the sheet 4c, and the sheet 4c is not limited to resin as long as it is sufficiently thinner (approximately L/20, for example) than a wavelength L of the acoustic wave received by the probe 1.

As described above, the holding plate 2 side of the acoustic matching member 4 is constituted by the sheet 4c, which is harder and less flexible than the water bag 4a. As a result, folded back creases are less likely to form in the sheet 4c. Hence, the sheet 4c can easily contact the holding plate 2 tightly without gaps, and therefore attenuation and reflection of the acoustic wave caused by creases can be suppressed, enabling an improvement in the quality with which the subject is measured. Further, the water bag 4a on the subject side of the acoustic matching member 4 is highly flexible and therefore tightly contacts the subject easily. As a result, folded back creases are less likely to form on the surface of the water bag 4a, and such creases can be plumped out by the water, sonar gel, and so on. Moreover, even when the holding plate 2 is curved, the sheet 4c can be brought into close contact with the curved surface thereof.

(Constitution and Materials of Acoustic Matching Member)

Next, the constitution and materials of the acoustic matching member 4 according to this example will be described in further detail.

Using FIG. 1B, a method of joining a urethane rubber sheet 4d directly to the sheet 4c will be described. With this method, the hollow portion can be formed, and as a result, the water bag 4a is manufactured.

By providing a matching agent supply line 4e, the matching agent can be filled into the interior of the water bag 4a following the joining operation, and the matching liquid can be replaced. When the water bag 4a is not provided with the matching agent supply line 4e, a method of partially joining the sheet 4c and the urethane rubber sheet 4d, filling the interior of the water bag 4a with the matching agent, and then joining the remaining part may be employed.

More preferably, a bellows 4f is provided such that a pocket containing a very small remaining amount of air is formed after the interior of the water bag 4a is filled with the matching liquid. When the water bag 4a is disposed at this time, the bellows 4f is provided in an opposite direction to a gravitational force of the water bag 4a. In so doing, the very small amount of air remaining after the matching liquid is charged can be stored in the bellows 4f. Further, the air pocket is not limited to the bellows 4f, and instead, for example, the urethane rubber may be molded into a tubular shape such that the air pocket is provided in a part of the water bag 4a.

Using FIG. 1C, a creation method employed when the sheet 4c and the urethane rubber sheet 4d are constituted by different materials such that a sufficient joint cannot easily be formed will be described. Note that supply of the matching agent and the air pocket are similar to those described using FIG. 1B and therefore description of these elements has been omitted.

Figure 1B:
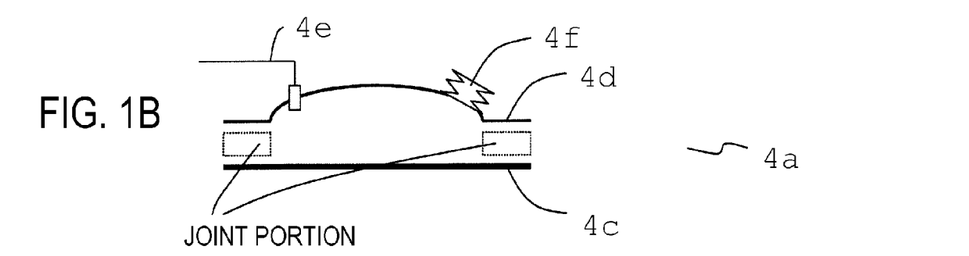
Figure 1C:
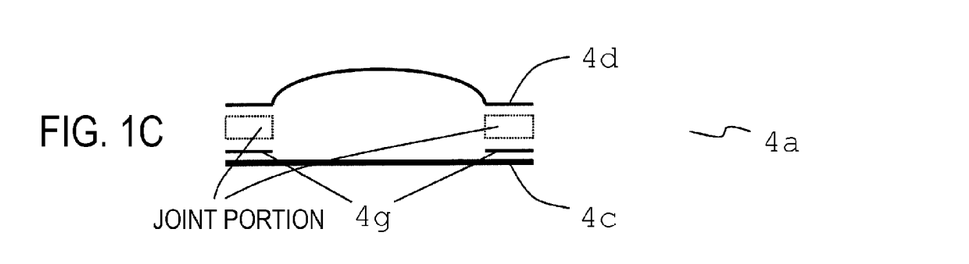

In FIG. 1C, a joint urethane rubber sheet 4g is adhered to the sheet 4c by an adhesive in at least a region to be joined to the urethane rubber sheet 4d. If, during adhesion, surface treatment is required on at least one of the sheet 4c and the joint urethane rubber sheet 4g, the surface treatment may be performed using a pre-existing method. By providing the joint urethane rubber sheet on the sheet 4c at the joint portion with the urethane rubber sheet 4d in this manner, identical urethane rubber sheets can be joined more easily. In FIG. 1C, the joint urethane rubber sheet 4g is provided only in the region of the joint portion, but the joint urethane rubber sheet 4g is equally effective when provided over the entire surface of the sheet 4c.

Figure 1D:
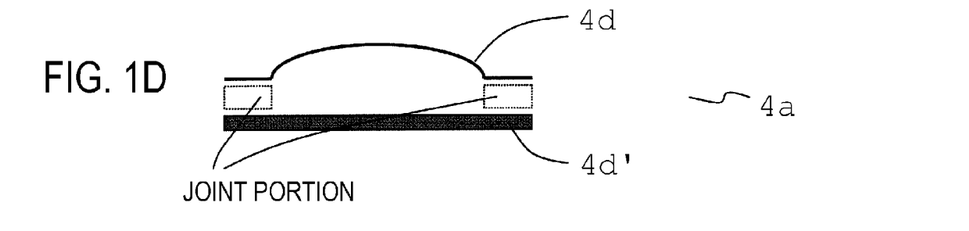

Furthermore, as shown in FIG. 1D, a thickness difference may be provided in the water bag 4a by employing a urethane rubber sheet 4d', which is made of an identical material to the urethane rubber sheet 4d but is thicker, instead of the sheet 4c shown in FIGS. 1B and 1C. Alternatively, a thick elastomer of a different type may be used. As a result, the (thick) urethane rubber sheet 4d corresponding to the sheet 4c is less flexible than the other parts, enabling a reduction in folded-back creases. The thickness should be set so that a restoring force which allows restoration from deformation under the sheet's own weight is obtained.

The joining methods described heretofore are preferably welding methods such as high-frequency welding. However, the joining methods are not limited to welding, and adhesion using an adhesive may be employed equally effectively.

As described above, at least one surface of the acoustic matching member 4 is constituted by a layer having greater rigidity than the other elastomer. Here, the greater rigidity indicates a higher Young's modulus, a smaller Poisson's ratio, or a higher hardness in a case where the materials are different. In cases where the materials are identical or the like, although the material itself is not more rigid, a highly rigid layer is formed by making the material thicker, and therefore less likely to deform in an out-of-plane direction, than the other elastomer. For example, when the thickness of the other elastomer (the urethane rubber sheet 4d) is approximately 30 μm (micrometer), a thickness of approximately 1 mm is appropriate.

Next, the materials of the respective parts will be described in further detail.

The material enclosed in the water bag 4a is preferably a liquid having water as a main component, but oil, a sol, or a gel may also be used.

The elastomer constituting the water bag 4a is preferably the urethane rubber sheet 4d. Either a polyether-based elastomer or a polyester-based elastomer may be applied to the urethane rubber sheet 4d. Hydrolysis occurs in polyester-based urethane rubber, but as long as the water bag 4a is used soon (within around several weeks, for example) after enclosing the liquid in the water bag 4a, the water bag 4a can be used safely, albeit with slight yellow discoloring. Other materials that can be used as substitutes include various types of rubber such as natural rubber (NR), and various types of vinyl such as polyvinyl alcohol (PVA).

The sheet 4c is preferably constituted by film-form PMP, but may be replaced with a resin having a tensile modulus of elasticity of 1000 MPa or more, such as polycarbonate (PC), polypropylene (PP), polyester, and polyethylene (PE). Further, as long as the sheet 4c is sufficiently thin relative to the wavelength L of the acoustic wave, the acoustic wave passes through the sheet 4c easily even when a difference in acoustic impedance exists. The thickness of the sheet 4c is preferably no more than L/20, for example. Hence, when a central wavelength of the acoustic wave is 1 MHz and an acoustic velocity through a living organism (the subject) is 1540 m/s, the wavelength L=1.54 mm, and therefore the thickness should be set at no more than 770 μm (micrometer) (L/20). The material may be substituted for a metal foil such as aluminum foil, or a non-metallic inorganic material such as glass or ceramic.

Further, a layer made of an identical material to the elastomer constituting the water bag 4a or a gel sheet 4b, or a layer made of a different type of elastomer having a higher hardness or a greater thickness, may be provided in place of the sheet 4c. The harder or thicker layer must be hard or thick enough to obtain a restoring force that allows restoration from self-weight deformation. Restoration from self-weight deformation denotes a restoring force for returning the member to its original shape from a bent state. When the rigidity of the material is too high to allow restoration from self-weight deformation, the material can be deformed easily by external forces, leading in particular to creases and surface irregularities. When the restoring force (a bending restoration property) is sufficient for achieving restoration from self-weight deformation, on the other hand, the surface of the material is self-correcting, and therefore creases and surface irregularities are less likely to occur. As a result, the tight contact property with the holding plate 2 improves, enabling acoustic matching in which air bubbles are less likely to infiltrate creases and surface irregularities. Note that the sheet 4c is not limited to the single material body described here and may be formed from multiple layers.

(Acoustic Matching Member Disposal Method)

Next, a method of disposing the acoustic matching member 4 in the subject information acquisition apparatus will be described.

Figure 3A:
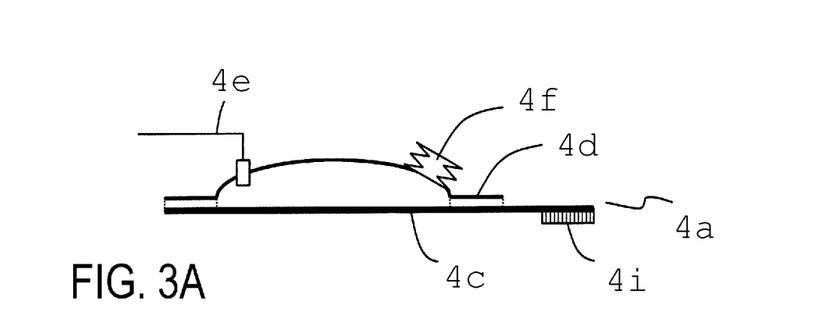
FIGS. 3A and 3B are views illustrating a method of disposing the acoustic matching member according to the present invention.
Figure 3B:
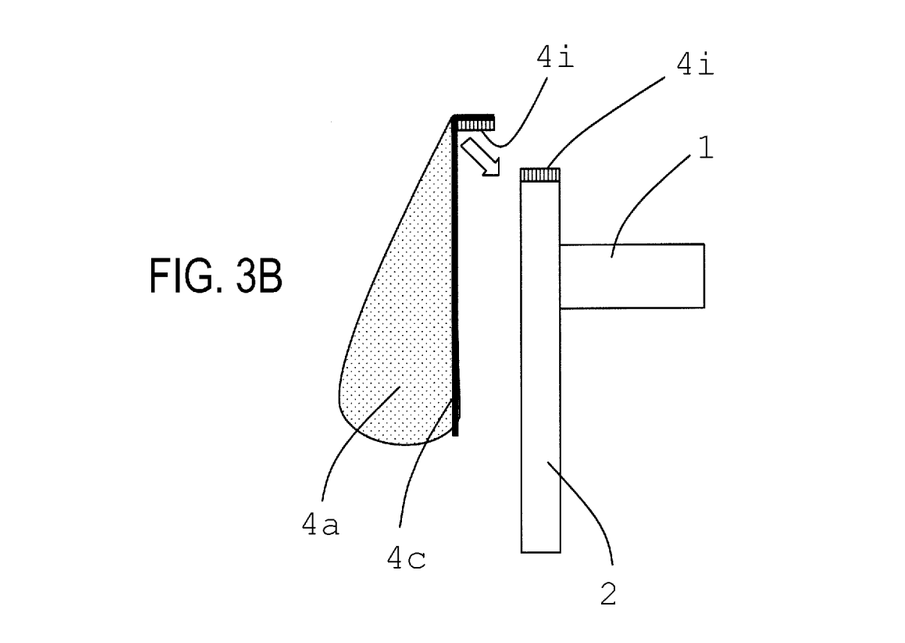

In FIG. 3A, a part of the sheet 4c shown in FIG. 1B is extended and provided with a hook-and-loop fastener 4i. To dispose this component in the apparatus shown in FIG. 1A, the hook-and-loop fastener 4i serving as an adhesion portion is provided on a part of the holding plate 2, whereupon the hook-and-loop fastener 4i of the water bag 4a is adhered to the hook-and-loop fastener 4i of the holding plate 2, as shown in FIG. 3B. In so doing, the acoustic matching member 4 can be disposed in the subject information acquisition apparatus so as to be repeatedly detachable. Note that in FIG. 3B, the hook-and-loop fastener 4i is provided on the holding plate 2, but the actual disposal method is not limited thereto, and for example, the acoustic matching member 4 may be made detachable by providing the hook-and-loop fastener 4i on a component in the vicinity of the holding plate 2.

As long as repeated detachment is possible, as with the hook-and-loop fastener 4i, a metallic hook may also be used on the adhesion portion. However, a hook-and-loop fastener or a similar component (for example, a pile-and-hook fastener or the like) is preferable for reducing discomfort caused when the hook impinges on the patient. FIGS. 3A and 3B show a combination of an apparatus employing the measuring method of FIG. 1A and the acoustic matching member 4 (the water bag 4a) of FIG. 1B. However, the combination of the measuring method of the apparatus and the acoustic matching member is not limited thereto.

By disposing the acoustic matching member 4 using the adhesion portion in this manner, the acoustic matching member can be replaced easily. Therefore, a hygienic apparatus in which the acoustic matching member is comfortable for each patient can be provided. Patient discomfort can be reduced particularly favorably when a hook-and-loop fastener is provided on the adhesion portion.

Example 2

Figure 2A:
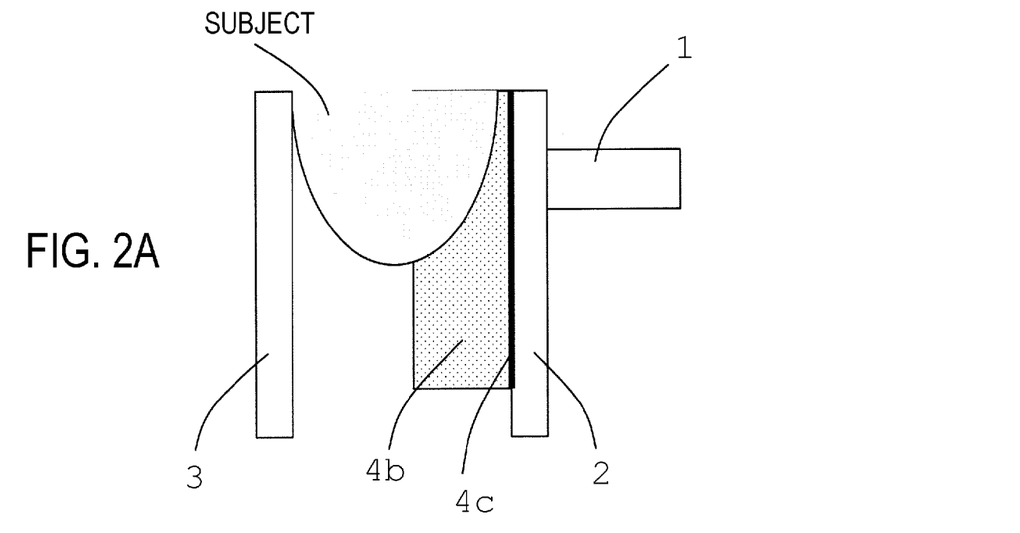
FIGS. 2A to 2C are views illustrating a constitution of an acoustic matching member according to a second example.

A second example will now be described. FIG. 2A is a pattern diagram of an apparatus according to this example. The apparatus shown in FIG. 2A differs from that of FIG. 1A in that the gel sheet 4b is used in place of the water bag 4a. The gel sheet 4b and the sheet 4c together constitute the acoustic matching member 4 according to this example. The gel sheet 4b contacts the subject, and the sheet 4c is positioned between the gel sheet 4b and the holding plate.

The gel sheet 4b is constituted by an elastomer, and a stand-off typically used in ultrasound diagnosis is appropriate. However, in order to fill gaps between the subject and the holding plate 2, the gel sheet 4b is preferably constituted by urethane gel having a Shore hardness of approximately 50. Note that the material and hardness of the gel sheet 4b are not limited to those cited above. The sheet 4c is constituted by an elastic body having greater rigidity (a higher Young's modulus) and a smaller Poisson's ratio than the gel sheet 4b. Suitable materials for the sheet 4c are similar to those cited in the first example.

Next, the constitution of the acoustic matching member 4 according to this example and a creation method thereof will be described.

Figure 2B:
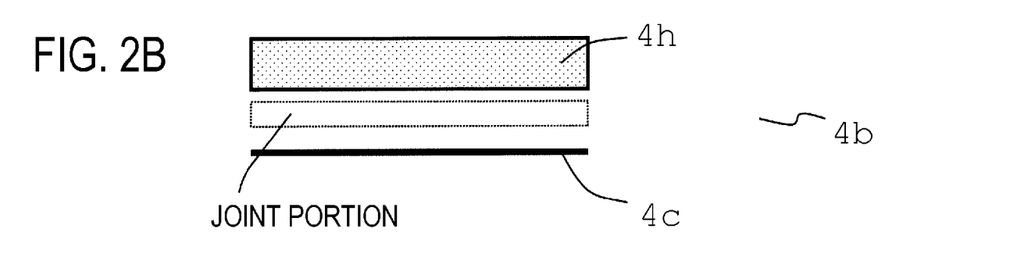

Using FIG. 2B, a method of joining a urethane gel 4h to the sheet 4c will be described. A material obtained by polymerizing a base compound having polyol as a main component, polyethylene glycol serving as a chain elongation agent, and denatured polyisocyanate serving as a hardener is a preferred example of the urethane gel 4h. However, the urethane gel 4h is not limited thereto, and another urethane gel or another elastomer such as a stand-off typically using in acoustic wave diagnosis may be applied thereto. The urethane gel 4h and the sheet 4c may be joined by adhesion using an adhesive or thermal welding, but since the surface of the urethane gel 4h is tacky, the urethane gel 4h and the sheet 4c may simply be brought into close enough contact to ensure that air does not infiltrate. If, at this time, the urethane gel 4h and the sheet 4c are brought into close contact via water or a liquid obtained by mixing a surfactant into water and the sheet 4c is rubbed from an opposite surface to the joint portion, infiltrating air can be removed together with the liquid. Alternatively, by using the sheet 4c as a die during pre-hardening, the urethane gel 4h and the sheet 4c are joined following hardening.

Figure 2C:
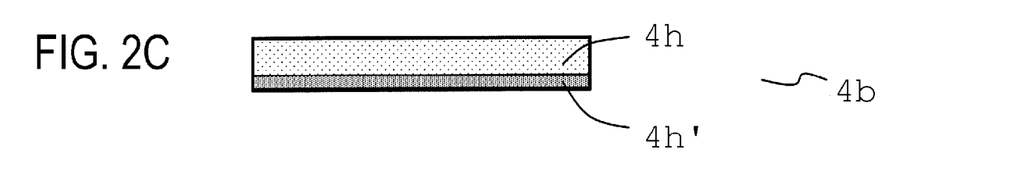

Further, as shown in FIG. 2C, a hardness difference may be provided in the urethane gel 4h. In FIG. 2C, the gel sheet 4b is created from the urethane gel 4h in a similar manner to FIG. 2B. A high-hardness part corresponds to the sheet 4c. To create the gel sheet 4b in this manner, a hardener concentration is differentiated when polymerizing the base compound having polyol as a main component, the polyethylene glycol serving as the chain elongation agent, and the denatured polyisocyanate serving as the hardener. For this purpose, the hardener is intermixed at a greater concentration on at least one surface, leading to an overall increase in hardness. In so doing, a part in which the hardness of the urethane gel 4h is low and a part in which the hardness of the urethane gel 4h is high can be formed in the interior of the gel sheet 4b. In this case, the Shore hardness of the low hardness side urethane gel 4h is set at approximately 50 and the Shore hardness of a high hardness side urethane gel 4h' is set at approximately 100. Note that the Shore hardness is not limited to these numerical values as long as the hardness is sufficient for obtaining a restoring force allowing restoration from deformation under the gel's own weight.

Alternatively, a low hardness urethane gel 4h and a high hardness urethane gel 4h may be created separately and then joined together as shown in FIG. 2C. Furthermore, different types of elastomers may be used.

Adhesion using an adhesive or thermal welding may be employed as the joining method, but since the urethane gel 4h itself is tacky, it is sufficient to bring the components into close enough contact to ensure that air does not infiltrate. If, at this time, the components are brought into close contact via water or a liquid obtained by mixing a surfactant into water, air infiltrating the joint surface can be removed.

As a result, the high hardness side urethane gel 4h is less flexible than the low hardness side urethane gel 4h, and therefore corresponds to the sheet 4c described with reference to FIG. 1 and FIGS. 1B to 2B. Hence, a hardness difference can be provided in the interior of the gel sheet 4b without using the sheet 4c. The urethane gel 4h described here is merely an example, and the present invention is not limited thereto. As long as a hardness difference is provided, other materials may be used.

Next, the materials of the gel sheet 4b will be described in further detail.

The urethane gel 4h is preferably used as the elastomer constituting the gel sheet 4b. The urethane gel 4h is preferably a material obtained by polymerizing a base compound having polyol as a main component, polyethylene glycol serving as a chain elongation agent, and denatured polyisocyanate serving as a hardener.

Polyether polyol, polyester polyol, polycarbonate polyol, and so on may be cited as examples of the polyol, but polyester polyol is preferably employed due to its durability. Condensed polyester polyol, lactone-based polyester polyol, ester modified polyol, and so on are preferably used as the polyester polyol. Of these materials, ester modified polyol in which a terminal of polyether polyol is modified by lactone is preferable due to its correlativity with the acoustic characteristics of the subject. Ethylene glycol, propylene glycol, trimethylolpropane, tetramethylene ether glycol, polyethylene glycol, and so on may be cited as the chain elongation agent. One type of chain elongation agent or a combination of two or more types may be used. Here, polyethylene glycol is preferable due to its correlativity with the acoustic characteristics of the subject. The isocyanate compound serving as the hardener is preferably a compound that can be matched to the acoustic characteristics of the human body. Examples of isocyanate compounds include hexamethylene diisocyanate (HDI), diphenylmethane diisocyanate (MDI), tolylene diisocyanate (TDI), isophorone diisocyanate (IPDI), xylylene diisocyanate (XDI), and so on.

Other materials that can be used as substitutes include various types of rubber such as natural rubber (NR), various types of vinyl such as polyvinyl alcohol (PVA), glucomannan, silicone, and so on.

When the acoustic matching member 4 is formed in the manner described above, the gel sheet 4b that contacts the subject is highly flexible, and therefore the acoustic matching member 4 can be brought into close contact with the subject favorably such that creases are unlikely to form on the surface thereof. Meanwhile, the sheet 4c contacts the holding plate 2 tightly without gaps, and therefore measurement can be performed while suppressing attenuation and reflection of the acoustic wave.

Moreover, when the acoustic matching member 4 is disposed on the holding plate 2 using a hook-and-loop fastener or the like, as described in the first example, the acoustic matching member can be replaced easily, and therefore a hygienic apparatus can be provided.

Example 3

Figure 6:
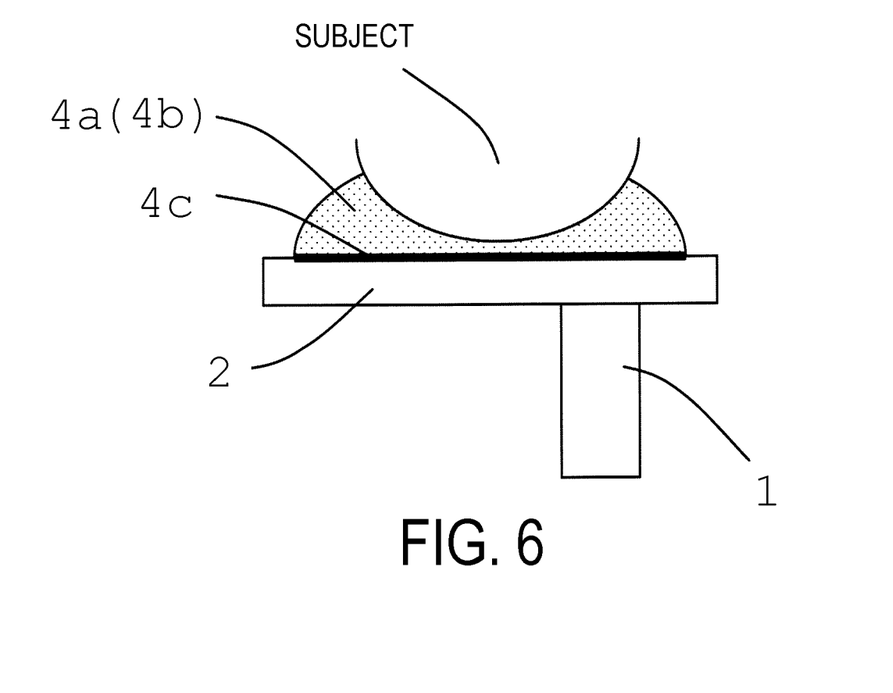
FIG. 6 is a view illustrating a constitution of an acoustic matching member according to a third example.

Next, a third example will be described. In the above examples, a method in which the subject is compressed and held from both sides is used, but as shown in FIG. 6, a measuring method in which the subject is pressed against the holding plate 2 may be used. In this case, the sheet 4c is disposed on the side of the acoustic matching member 4 that contacts the holding plate, and the water bag 4a or the gel sheet 4b is disposed on the side that contacts the subject. Likewise with this constitution, creases in the acoustic matching member can be suppressed, and reductions in measurement quality due to attenuation and reflection caused by creases can be prevented.

Furthermore, the attitude of the subject is not limited to a face-down attitude, and a method in which the measurement site is compressed and held after placing the subject in a different position such as a standing position or a sitting position, for example, may be employed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-021169, filed on Feb. 2, 2010, which is hereby incorporated by reference herein in its entirety.

The invention claimed is:

1. A subject information acquisition apparatus comprising:
 a pair of holding plates adapted to hold and sandwich a subject;
 an acoustic matching member provided on one of said holding plates and having a flexible bag and an acoustic matching agent stored in the flexible bag; and
 a probe adapted to be positioned to receive acoustic waves from the subject, said probe being located in opposition to said acoustic matching member with said one of the pair of holding plates between said probe and said acoustic matching member,
 wherein said flexible bag has a first portion facing the other of the pair of holding plates adapted to contact the subject and a second portion detachably secured to said one of the pair of holding plates, the second portion having higher rigidity than the first portion,
 wherein both said first portion and said second portion are located on an acoustic wave propagation path such that acoustic waves are adapted to be propagated from the subject to said probe through said first portion, said acoustic matching agent and said second portion in that order, and wherein said first portion and said second portion are made of the same material, and said second portion has a thickness greater than that of said first portion to provide said higher rigidity.

2. The subject information acquisition apparatus according to claim 1, wherein said acoustic matching agent includes at least one of a liquid, a sol, and a gel between said first portion and said second portion.

3. The subject information acquisition apparatus according to claim 1, wherein said flexible bag contains an elastomer.

4. The subject information acquisition apparatus according to claim 1, further comprising a light source that is configured to irradiate the subject with light to cause a photo-acoustic wave to be generated from the subject.

5. The subject information acquisition apparatus according to claim 1, wherein said probe is controlled to emit ultrasound, and is adapted to receive an acoustic wave that is an ultrasonic wave emitted by said probe and reflected in the subject.

6. The subject information acquisition apparatus according to claim 1, wherein said one of said pair of holding plates and said second portion each have hook-and-loop fasteners.

7. The subject information acquisition apparatus according to claim 1, wherein a rigidity difference between said first portion and said second portion is such that said first portion contacts the subject in conformal manner even where the subject has an uneven profile.

8. The subject information acquisition apparatus according to claim 1, wherein a rigidity difference between said first portion and said second portion is such that occurrence of a residual air gap at an interface between said second portion and said one of the pair of holding plates is restricted.

9. The subject information acquisition apparatus according to claim 1, wherein said first portion is spaced from said one of the pair of holding plates by said second portion, and wherein said probe is adapted to receive an acoustic wave from the subject by the acoustic wave passing to said probe from said first portion through said second portion and said one of the pair of holding plates.

10. The subject information acquisition apparatus according to claim 1, wherein contact between said flexible bag and said one of the pair of holding plates is defined by at least a region of said second portion.

11. The subject information acquisition apparatus according to claim 1, wherein said second portion lies substantially flat on said one of said pair of holding plates, and spaces said first portion from said one of said pair of holding plates.

12. A subject information acquisition apparatus comprising:

a pair of holding plates adapted to hold and sandwich a subject;

an acoustic matching member provided on one of said holding plates and having a flexible bag and an acoustic matching agent stored in the flexible bag; and a probe located in opposition to said acoustic matching member with said one of the pair of holding plates between said probe and said acoustic matching member, wherein said flexible bag has a first portion facing the other of the pair of holding plates adapted to contact the subject and a second portion detachably secured to said one of the pair of holding plates, the second portion having higher rigidity than the first portion, wherein said first portion and said second portion are made of the same material, and said second portion has a thickness greater than that of said first portion to provide said higher rigidity, and wherein both of said first portion and said second portion are located on an acoustic wave propagation path such that acoustic waves are adapted to be propagated from the subject to said probe through said first portion, said acoustic matching agent and said second portion in that order.

13. The subject information acquisition apparatus according to claim 12, wherein said second portion has at least one of size and shape such as to restrict said second portion from introducing generation or reflection of acoustic waves by said second portion during transmission of acoustic waves from said flexible bag to said probe.

\* \* \* \* \*